(12) United States Patent
Simo et al.

(10) Patent No.: US 6,305,400 B1
(45) Date of Patent: Oct. 23, 2001

(54) MEDICAL GAS EMERGENCY DELIVERY SYSTEM AND METHOD

(75) Inventors: Donald M. Simo, Vermilion; James L. Lucas, Jr., Elyria, both of OH (US)

(73) Assignee: Tri-Tech Medical Inc., Avon, OH (US)

( * ) Notice: Subject to any disclaimer, the term of this patent is extended or adjusted under 35 U.S.C. 154(b) by 0 days.

(21) Appl. No.: 09/643,703

(22) Filed: Aug. 22, 2000

(51) Int. Cl.$^7$ ..................................... F16K 11/22
(52) U.S. Cl. ........................ 137/14; 137/360; 137/382; 137/606
(58) Field of Search ................. 137/597, 382, 137/360, 606, 1, 14; 251/89

(56) References Cited

U.S. PATENT DOCUMENTS

| | | | |
|---|---|---|---|
| 4,422,314 | * 12/1983 | Cooper | 137/382 |
| 4,546,794 | * 10/1985 | Ball | 137/599 |
| 4,989,637 | * 2/1991 | Dittrich | 137/606 |
| 4,991,820 | * 2/1991 | Kohn et al. | 251/149.5 |
| 5,435,342 | * 7/1995 | Kohn et al. | 137/360 |
| 5,522,420 | * 6/1996 | Martin | 137/382 |
| 5,950,675 | * 9/1999 | Minami et al. | 137/606 |

* cited by examiner

*Primary Examiner*—Stephen M. Hepperle
(74) *Attorney, Agent, or Firm*—Christopher L. Parmelee; Ralph E. Jocke; Walker & Jocke

(57) ABSTRACT

A system and method for connecting a secondary source of a medical gas to a medical gas supply system which enables uninterrupted gas supply without backfeeding. A control panel (10) is connected in the system fluidly between primary supply sources (44, 45, 46) holding types of medical gas and gas outlets (54, 55, 56) for the delivery of the respective types of medical gas to devices in a medical facility. For each gas type the control panel houses a respective shut off valve (24, 25, 26). The shut-off valve may be closed to isolate the upstream source from the downstream components. The control panel also houses for each gas type a respective secondary gas inlet port (68, 69, 70). The inlet ports have connections specific to the type of gas which may be received therethrough. Check valves are provided to enable fluid flow only into the inlet ports. A removable cover or face (11) is normally installed on the control panel. The face can only be installed when the shut-off valves are all open. To connect a secondary gas source the face is removed from the control panel. The respective shut-off valve is closed and a secondary source of medical gas is fluidly connected to the appropriate inlet port to maintain the supply of gas.

17 Claims, 7 Drawing Sheets

MEDICAL GAS EMERGENCY DELIVERY SYSTEM AND METHOD

TECHNICAL FIELD

This invention relates to the supply of medical gases in the environment of a medical facility. More specifically, this invention is concerned with connecting a secondary gas supply to a medical gas supply system in a safe and efficient manner in the event that the primary supply is unable or unsuitable to deliver gas as required.

BACKGROUND ART

It is often necessary for trained personnel to provide a variety of gases of medical quality in a medical facility. Examples of such gases include medical air, oxygen, nitrogen, nitrous oxide, and carbon dioxide. Systems are also often installed in medical facilities which provide vacuum or gas evacuation. Gas service may be provided through a system which delivers the gas throughout a facility or portions or zones thereof. A number of primary supply sources of gas are used to deliver gas through outlet ports positioned at locations within the medical facility. The delivery system for each type of gas commonly includes manifolds with appropriate shut-off valves and pressure gauges. The delivery system also commonly includes at least one pressure regulator, check valve, and piping supply lines connecting the elements of the system. The primary supply source for each gas may be located in a secure area in the interior of the medical facility. Alternatively a primary supply source may be located at the exterior of the facility for maintenance by outside vendors providing the various gases.

It is critically important that the correct gas at the proper pressure be supplied when required from a medical gas supply system. Great effort is taken to assure that the various gases supplied are clearly marked at all locations. The possibility for delivery of the wrong gas at an incorrect location should be minimized. The pressure of each gas delivered may also be appropriately monitored throughout the system.

There are occasions which may require a secondary gas source to be connected to the gas delivery system of a medical facility. These instances might involve an emergency, a need for maintenance, a requirement of inspection, certification testing or service. One method of connecting the secondary gas source involves connecting the secondary gas source to the system through a hose to a conduit in the facility which normally serves as an outlet. Such an arrangement, known as backfeeding in the industry, is unacceptable according to the National Fire Protection Association (NFPA), the regulatory agency responsible for medical gas piping standards. Such a connection, according to NFPA, puts the system and possibly users thereof at risk of injury or damage.

Gases delivered by medical gas systems are generally at relatively low pressures. Typical desired pressure levels are 50 psi for oxygen, nitrous oxide, carbon dioxide and medical air, 180 psi for nitrogen, and 15 in/Hg to 25 in/Hg for vacuum or gas evacuation. Bottled gases by comparison have considerably higher pressures, commonly about 2000 psi. If the wrong gas were delivered to the wrong supply line through backfeeding, incorrect pressure or flows in portions of the system may occur. Such incorrect pressures and flows may place equipment and personnel at risk.

The medical system for each gas type is designed to provide gas flow from the primary source toward the various outlets and devices which utilize the gas within the medical facility. Gas should not be allowed to flow in a direction opposite to that for which the equipment was designed. Reverse operation requires a user to thoroughly understand every component of the system and what is necessary to safely accomplish reverse flow. It is often difficult to conduct such an analysis when many types of devices may be connected to the system.

For these reasons NFPA has disapproved of the practice of backfeeding of gas supply lines. Despite the NFPA position, personnel in medical facilities when faced with the necessity of keeping gas systems in operation are forced to use such backfeeding connections. In 1996 NFPA took the position that emergency service of an oxygen supply could be provided by a low pressure inlet located in the main supply line. This inlet is required to be located at the exterior of the medical facility. The use of such an inlet is authorized only for use to achieve an emergency supply of oxygen and is not to be used in the case of inspection/certification. Since this emergency inlet port is not required to be retrofit into existing "grandfathered" systems, most medical facilities are not equipped with this capability. Such an arrangement is of no help when the problem in the system is something other than the main supply, such as a system break inside the medical facility. In addition, gas delivery systems are normally divided into zones. This port does not allow gas service to be selectively supported or inspection/certification activities to be performed by selected zones. As a result, even in oxygen systems which have such a port the practice of backfeeding is sometimes necessary.

Thus there exists a need for an apparatus and method for connecting a secondary supply of a medical gas to a medical gas supply system. There further exists a need for an apparatus and method of connecting such a secondary supply of medical gas in a quick and reliable manner, which can be connected to selected zones of the supply system and which does not require backfeeding of any portion of the gas supply system.

DISCLOSURE OF INVENTION

It is an object of the present invention to provide a method of connecting a secondary gas source to a medical gas delivery system.

It is a further object of the present invention to provide a method which enables medical or service personnel to connect a secondary gas source to a medical gas delivery system for emergency and service purposes.

It is a further object of the present invention to provide a method for connecting secondary sources of medical gases to a medical gas delivery system without backfeeding of portions of the medical gas supply system.

It is a further object of the present invention to provide a method that enables a secondary supply source of a medical gas to be rapidly and reliably connected to a medical gas supply system.

It is a further object of the present invention to provide a method that enables a secondary supply source of a medical gas to be connected to selected zones of a medical gas supply system.

It is a further object of the present invention to provide a method of connecting a secondary supply source of a medical gas to a medical gas supply system which reduces the risk of incorrect connections.

It is a further object of the present invention to provide an apparatus for reliably and quickly connecting a secondary supply source of a medical gas to a medical gas delivery system.

Further objects of the present invention will be made apparent in the following Best Mode for Carrying Out the Invention and the appended claims.

The foregoing objects are accomplished in an exemplary embodiment of the invention by a method of connecting a secondary gas source to a medical gas supply system in a medical facility. Gas piping carries each gas from a primary supply source, through supply lines and to various outlets and devices in the medical facility or portions thereof. A control panel is positioned in a main supply line. The main supply line may supply the entire system or a portion or zone within the system. The control panel houses a shut off valve which when closed separates the primary supply source from the balance of the system. Also housed within the control panel is an inlet port for connection to a secondary gas supply. The inlet port is fluidly connected to the system downstream of the valve. Access to the valve and the inlet port in the control panel is normally prevented by a removable face on the control panel. The control panel is constructed so that if the removable face is in position on the control panel it is required that the valve is in an open condition so that the system is being supplied from the primary gas supply source.

In situations when it is necessary to supply the system or a respective zone controlled from the control panel from a secondary gas supply source, the face of the control panel is removed. The valve in the interior of the control panel is closed. This isolates the primary supply source and other system components upstream of the control panel from the system and devices downstream of the control panel. The secondary gas supply source is connected to the inlet housed in the control panel. Gas from the secondary source is allowed into the system in a controlled fashion through the inlet to maintain the gas supply to downstream components. This inlet port is preferably provided with a specific threaded coupler using a diameter indexed safety system (DISS). Only a mating specific threaded coupler can be connected to the port. This arrangement increases the probability that only a secondary gas source suitable to use in the system can be connected to a specific inlet port.

BEST MODES FOR CARRYING OUT INVENTION

Figure 1:
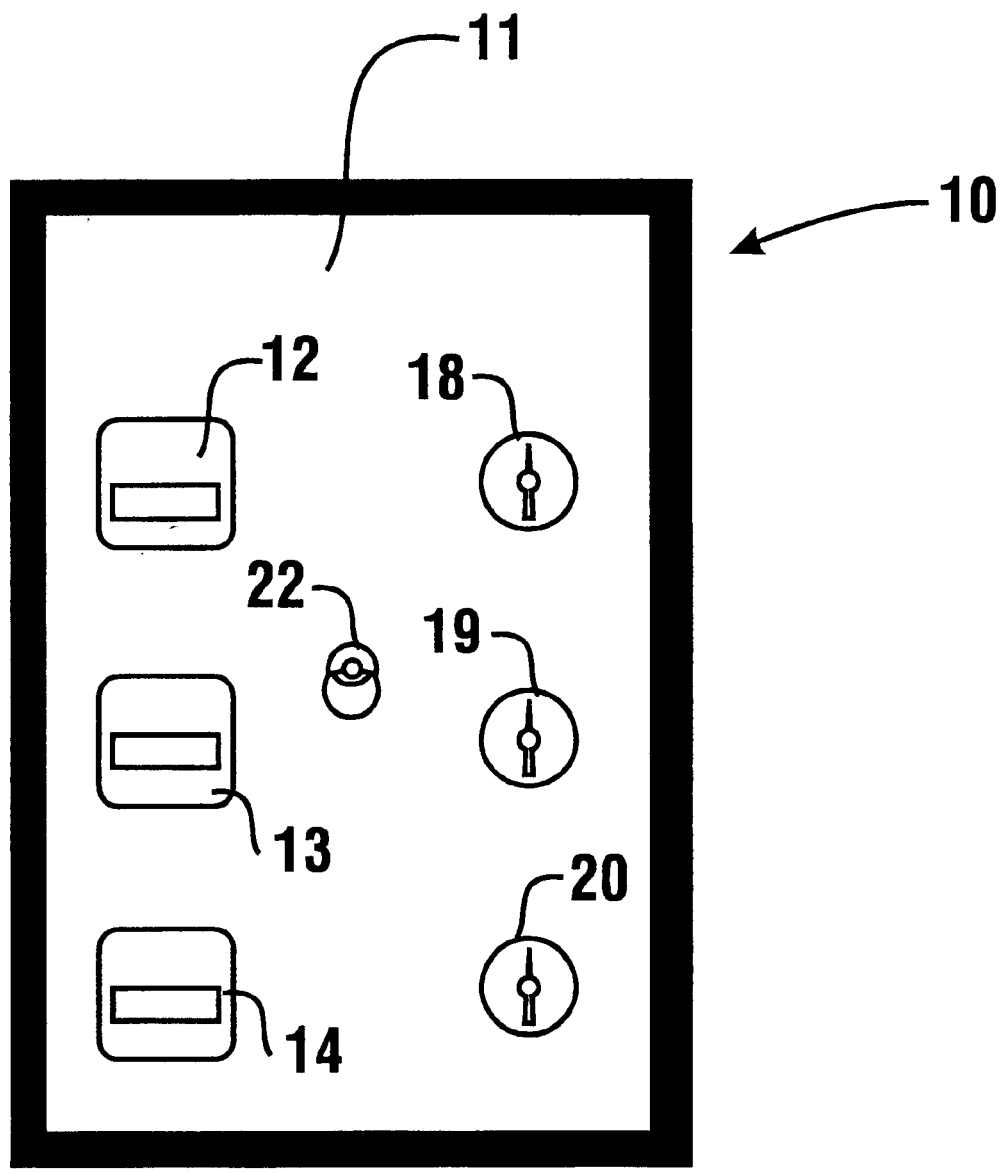
FIG. 1 is a plan view of a control panel for zone shut-off valves in a medical gas supply system.

Referring now to the drawings and particularly to FIG. 1 there is shown therein a control panel 10. Control panel 10 is designed to be installed in a medical gas supply system in a medical facility which employs an exemplary embodiment of the present invention. The panel 10 includes a face 11. Panel 10 is designed to accommodate controls and fluid connections for three separate gases. Each control panel installation in a gas supply system may need to accommodate more or less than three gases. The control panel may be specifically designed for the number of gases required to flow therethrough. In the exemplary embodiment face 11 has gas identification placards 12, 13 and 14 for each gas which passes therethrough. The gas identification placards 12, 13 and 14 preferably include specific markings and indicia which indicate the particular medical gas which flows in each line and the area of the facility served by each valve.

In the exemplary embodiment of control panel 10 faces of pressure gauges 18, 19 and 20, one for each gas, are visible through the face 11. Pressure gauges 18, 19 and 20 monitor pressure at the control panel location in the system. Gas types commonly provided through the use of panel 10 in a medical facility include medical air, oxygen, nitrogen, nitrous oxide, carbon dioxide and vacuum or gas evacuation. In the case of oxygen, nitrous oxide, carbon dioxide and medical air, the pressure gauge face commonly reads in a range from 0 to 100 psi. For nitrogen the gauge face commonly reads in a range from 0 to 300 psi. For vacuum or gas evacuation the gauge face reads in a range from 0 to 30 in/Hg. It should be understood that while in the exemplary embodiment gauges are used as pressure indicators, in other embodiments other types of pressure indicating devices may be used. The frame of the face 11 of the panel is attached by screws which releasably secures the frame of the face to the control panel 10. In the exemplary embodiment the face may be removed from the panel by pulling on a ring 22. The face of the control panel is reinstalled by moving the panel into position. In embodiments of the invention various releasable latching mechanisms may be used to secure the face to the control panel.

Figure 2:
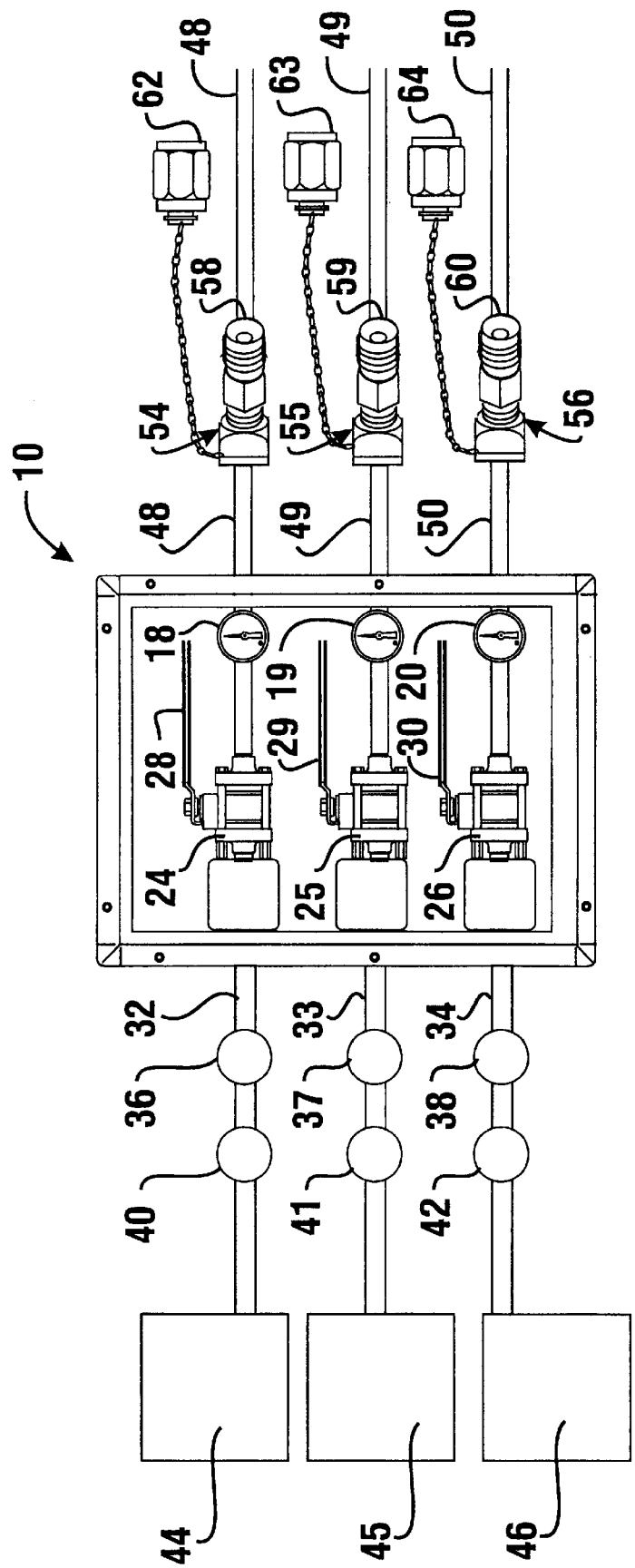
FIG. 2 is an exemplary schematic diagram representative of a medical gas supply system.

FIG. 2 illustrates the control panel 10 installed in a simplified exemplary embodiment of a medical gas delivery system. Face 11 of the panel has been removed to reveal the contents thereof. Pressure gauges 18, 19 and 20 are located within the enclosure of panel 10. Additionally, shut-off valves 24, 25 and 26, one for each of the gas lines, are housed within the panel. The pressure gauges are positioned in the panel on the downstream side of the valves.

The shut-off valves 24, 25 and 26 in the exemplary embodiment are preferably three-piece in-line repairable ball type valves. In the exemplary embodiment they are constructed of bronze and have Teflon® seats and seals. The valves are commonly rated at 600 psi. Each valve includes adjustable packing and a blowout proof stem. Valves 24, 25 and 26 are operated by lever handles 28, 29 and 30. Operation of the valve from fully open to fully closed requires only one quarter of a full turn of the handle. The control panel is preferably constructed so that the handle extends outward when in the closed position. As a result the face must be removed from the panel when a valve is in a closed position. This is useful in enabling quick visual inspection of the conditions of the valves.

A control panel 10 is preferably used as part of a gas feed system zone manifold in a plurality of zones required throughout the medical facility. The facility is sectioned into zones requiring similar gases or uses with a valve locked open controlling the supply of gas to each zone. Control panels may also be positioned for specific sub-zones or areas within the facility. The zone arrangement simplifies inspection and maintenance in that only a specific zone could be incapacitated or require gas delivery from a secondary source. By pulling the ring 22 and removing face 11 of the control panel, one or more shut-off valves 24, 25 or 26 within the panel are enabled to be closed. By closing the appropriate valve a particular zone or line in the system could be isolated without interfering with the balance of the gas delivery system.

The exemplary control panel 10 includes primary source inlets 32, 33 and 34 upstream of the shut-off valves 24, 25 and 26. Each gas line in the system also preferably includes a check-valve 36, 37 and 38 which are connected upstream of the respective inlet 32, 33 and 34. The check-valve assures that gas under pressure does not flow in a reverse direction within the system. Pressure regulators 40, 41 and 42, one for each gas supply line, are connected upstream of the respective check-valve 36, 37 and 38. The pressure regulators are adjusted to supply the particular gas within the desired pressure ranges as noted above.

A primary gas source 44, 45 and 46, is connected upstream of the respective pressure regulator 40, 41 and 42. One primary gas source is provided for each of the gases the system is to deliver. In an exemplary embodiment each primary gas source 44, 45 and 46 may include a pressure vessel accessible from the exterior of the facility. The primary gas sources are therefore readily available to agents of an outside vendor for the purpose of servicing and refilling. In alternative embodiments other primary sources such as compressors, oxygen concentrators or other devices which produce or deliver the medical gas may be used. In systems which supply vacuum, an appropriate vacuum pump or similar device is connected to a respective line.

The control panel 10 has outlets 48, 49 and 50 located downstream of the pressure gauges 18, 19 and 20. These outlets connect the control panel to the balance of the gas delivery system within the zone or other area controlled by the control panel. Outlet ports 54, 55 and 56 are shown connected to outlets 48, 49 and 50, respectively. These outlets are representative of a plurality of outlets that may be connected to the gas system in the zone controlled by panel 10. All of the individual elements of the gas delivery system are interconnected with appropriate piping. In the exemplary embodiment each outlet port 54, 55 and 56 includes a gas specific diameter indexed safety system (DISS) threaded coupler 58, 59 and 60. In such a system only a unique fitting size and/or coupling type is used in connection with each medical gas. These gas specific sizes and/or coupling types provide increased assurance that only the correctly mating gas apparatus is connected to the line.

In the exemplary system shown a mating threaded closure or cap 62, 63 and 64 is located closely adjacent to the respective coupler. The caps are preferably attached to an area adjacent each outlet port 54, 55 and 56 through the use of a chain or wire. This reduces the risk that a removed cap will be lost. Although shown unthreaded for purposes of clarity of description, caps 62, 63 and 64 must be engaged on threaded outlet ports 58, 59 and 60 whenever an apparatus is not engaged to the outlet. This arrangement minimizes the risk that foreign matter enters an outlet port 54, 55 and 56 to cause contamination of the system.

During normal conditions each required medical gas type is available at each primary gas source 44, 45 and 46 and the shut-off valves 24, 25 and 26 in the control panel are open. Medical personnel can access a particular gas line as needed. This is accomplished by attaching a desired apparatus to an outlet port 58, 59 or 60. Gas flows in the desired direction only from the source to the outlets at the proper pressure for the gas utilizing devices connected to the system.

In the event of a system failure in which any element of the system upstream of shut-off valve 24, 25 or 26 fails or requires service, face 11 of the control panel 10 is removed by pulling on the ring 22. The appropriate shut-off valve 24, 25 or 26 for the gas type involving the failure may then be closed. This would be the case if a primary gas source 44, 45 or 46 became empty or another system component upstream of the control panel malfunctioned. The appropriate shut-off valve 24, 25 or 26 is closed so the system is not contaminated and there is no flow backward toward the primary supply source. Closing the valve in the control panel also isolates the zone downstream of the control panel from the remainder of the system.

Figure 3:
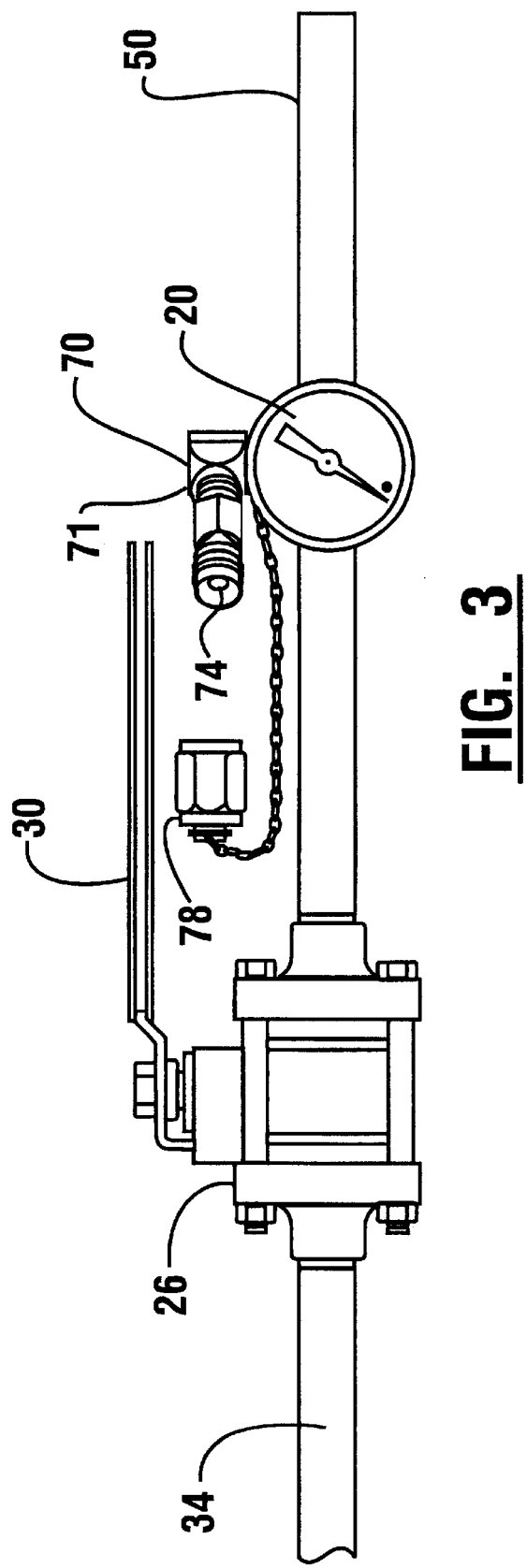
FIG. 3 is an exemplary schematic diagram representative of a manifold portion of the medical gas supply system including an inlet port.

In an exemplary embodiment of the invention, shown in FIG. 3, an inlet port 70 is connected in a gas conduit adjacent pressure gauge 20 within the control panel. The inlet port 70 preferably has a gas specific DISS threaded coupler 74 incorporating a demand check valve. A mating gas specific threaded closure or cap 78 serves to secure the inlet port when not in use to minimize the risk of contamination and provide additional protection from possible gas leakage. The cap 78 may be secured to inlet port 70 by a chain or wire when not in use. A check valve 71 is connected to inlet port 70 for the purpose of assuring that pressurized gas may only flow in a direction into the inlet port 70 and serve as a primary seal when the system is in normal use. When shut-off valve 26 is closed, inlet port 74 may be used to supply the zone downstream of the control panel with gas from a secondary supply source.

Figure 4:
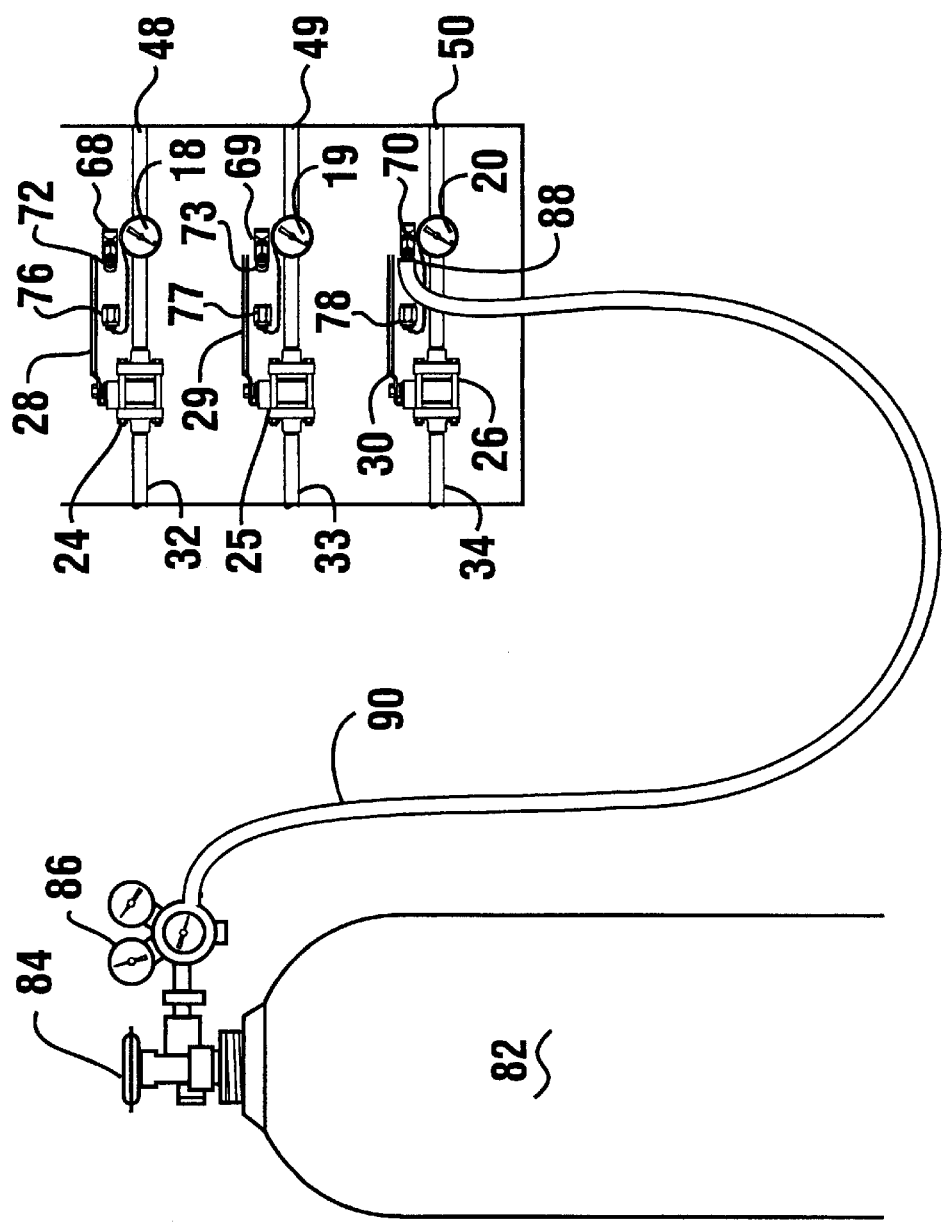
FIG. 4 is an exemplary schematic diagram representative of the manifold portion of the medical gas supply system including a secondary gas supply connected to the inlet port.

FIG. 4 shows a secondary source of gas, including a pressure vessel 82, connected to the inlet port 70 in the control panel 10. The secondary gas source includes a valve 84 and regulator 86 which control the pressure at which gas is delivered. The pressure vessel 82 is connected to deliver gas to inlet port 70 through a mating gas specific DISS threaded coupler 88. Coupler 88 in the embodiment shown is at the end of a hose 90 leading from regulator 86 of the secondary gas source. Once the proper connection of pressure vessel 82 to inlet port 70 has been made, valve 84 is opened to establish the fluid connection with the secondary source. Gauge 20 on the control panel provides an indication that the secondary source is supplying gas at the appropriate pressure. The secondary source supplies gas on an interim basis through the inlet port without backfeeding any portion of the system. As a result gas flows in the normal manner to all devices connected in the system downstream of the shut off valves 24, 25 and 26.

In the exemplary embodiment inlet ports 68, 69 and 70 are connected to respective gas conduits in the control panel adjacent pressure gauges 18, 19 and 20. Each inlet port 68, 69 and 70 includes a gas specific DISS threaded coupler 72, 73 and 74 to minimize the risk of an incorrect connection. Mating caps 76, 77 and 78, respectively, correspond to the gas specific threaded coupler 72, 73 and 74 on the inlet ports to close the inlet ports when not in use. The control panel enables connecting a secondary source of gas for each gas type used in the system. Multiple gas sources and gas types may be connected through a single control panel.

The explanation herein has centered around maintaining gas supply despite a depleted or inoperative primary source of gas. In the event that maintenance, inspection or certification of a portion of the gas delivery system is required, a secondary gas source could be connected. Secondary gas sources may be used to supply selected zones which are isolated by the shut off valves from other zones. The check valves associated with the inlet for the secondary gas source assures that the primary and secondary sources may be connected and disconnected through the control panel in a manner that provides an uninterrupted supply of gas to the zone and which avoids loss of gas or damage to the system.

When gas flow from the primary source is to be restored, the shut-off connecting the gas source in the control panel may again be opened. The valve from the secondary source is then closed and the connection to the secondary inlet in the control panel disconnected. A demand valve in item 74 or 58, 59 and 60 automatically closes preventing any escape of gas. The cap on the inlet is then installed. The face may then be attached to the control panel to indicate that all the valves within the panel are open.

The exemplary embodiment of the present invention may also be used to facilitate the introduction of purging gases into a portion of the medical gas system. When additions or maintenance to medical gas systems are performed, NFPA 99 requires that purging gases such as nitrogen be placed into the medical gas pipeline prior to brazing. The purging gas reduces the formation of copper oxide during the brazing process by removing oxygen and moisture from the pipeline. In the exemplary embodiment the secondary input ports 68, 69, 70 provide readily available ports through which a purge gas may be input into the system.

Figure 5:
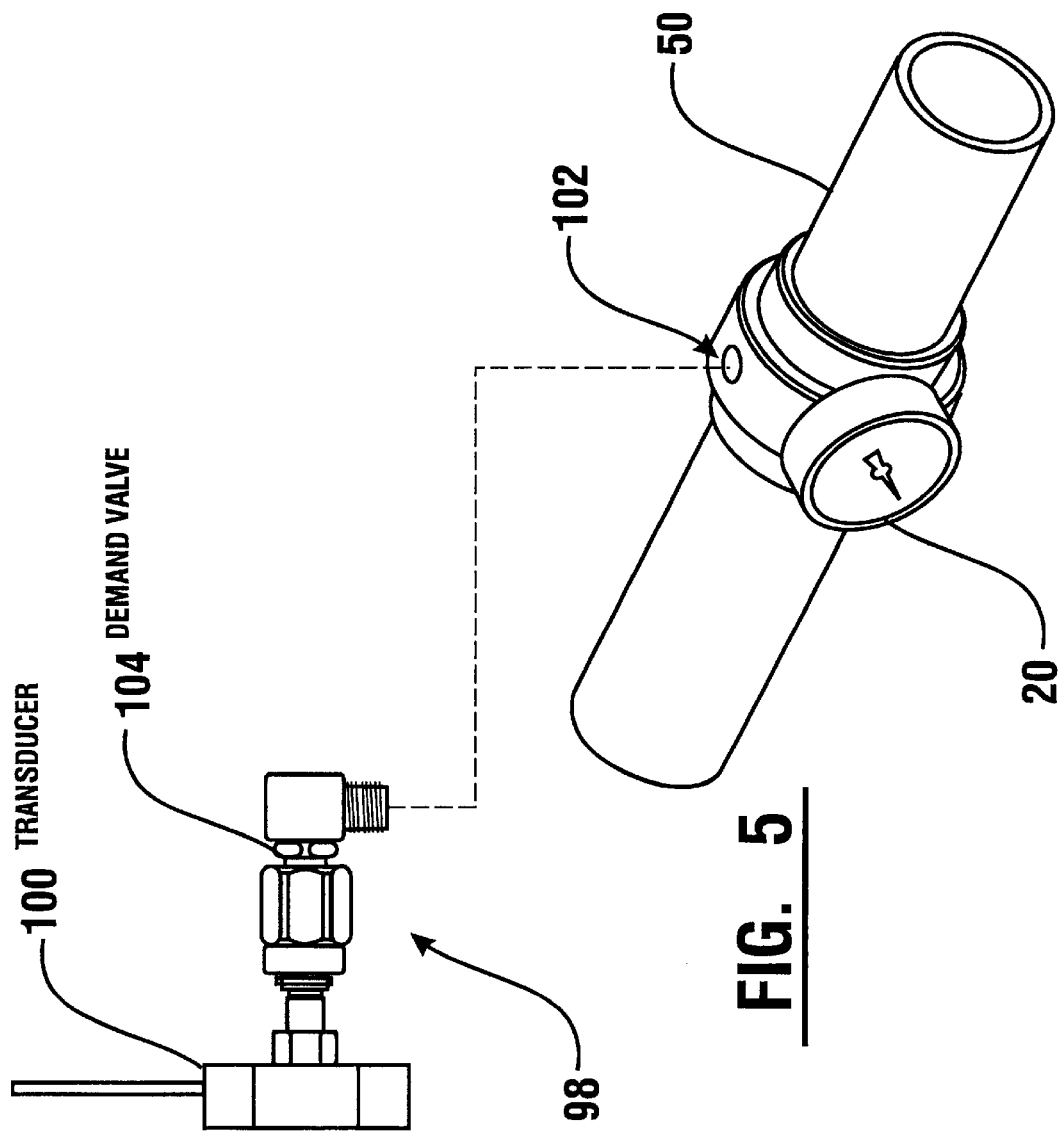
FIGS. 5 and 6 are exemplary schematic diagrams representative of connecting a transducer to the secondary gas inlet port of the medical gas supply system.

In addition to providing a gas specific secondary inlet for medical and purge gases, the exemplary embodiment of the control panel 10 may also be used for the remote connection of monitoring transducers. FIG. 5 shows a transducer assembly 98 being placed in connected with the inlet port 70. Here the transducer assembly includes at least one transducer 100 which is operative to remotely monitor properties of gases in the system. In the exemplary embodiment the transducer assembly further includes a demand check valve 104 which is operative to prevent outside gases and other contaminants from entering the system when the transducer is installed, repaired or replaced.

Figure 6:
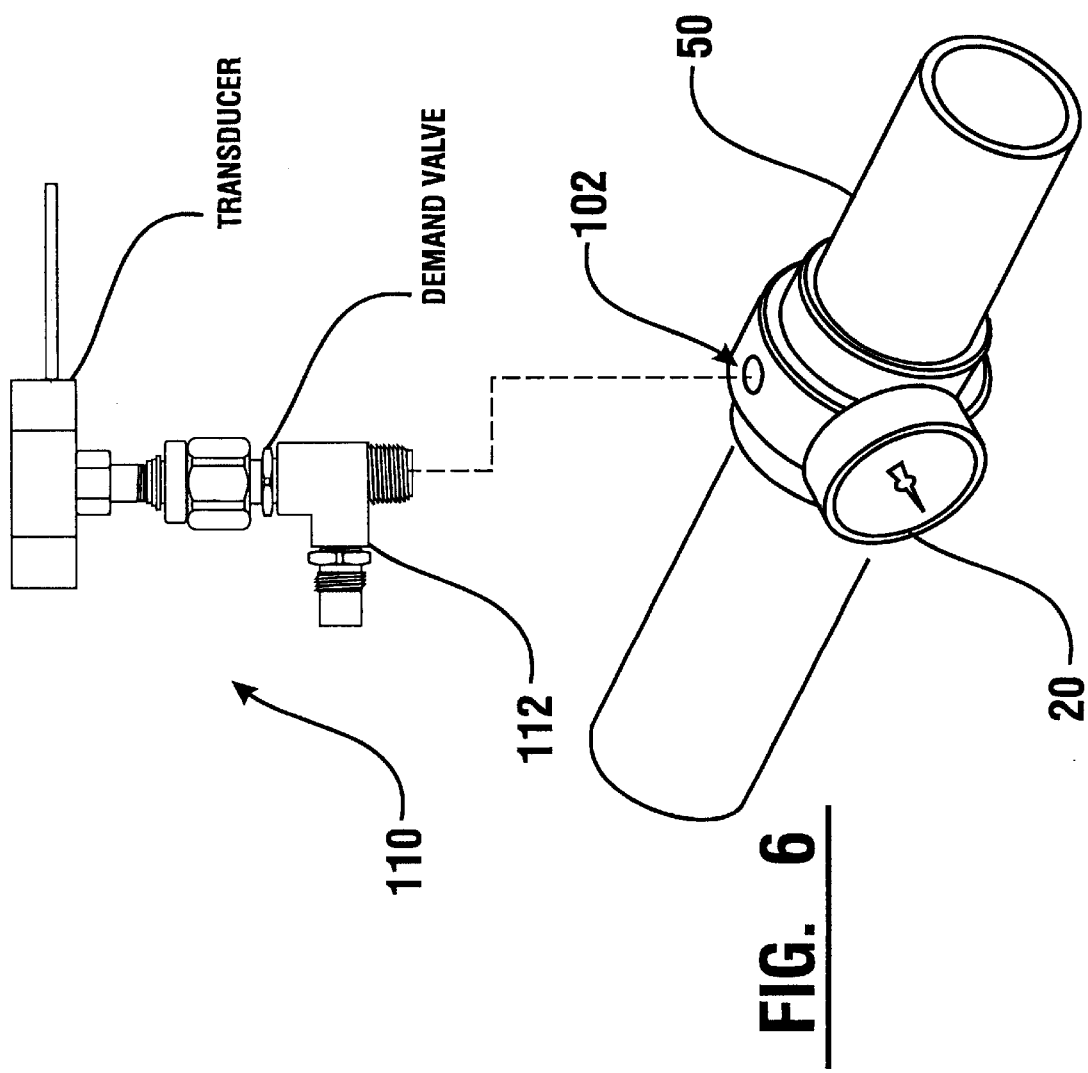

FIG. 6 is representative of an alternative transducer assembly 110, which includes a second connection end 112. The second connection end 112 enables the connection of addition transducers to the manifold. In addition the second connection end 112 can be configured to accept a secondary gas source by including a demand check valve and a DISS threaded coupler as previous described.

Figure 7:
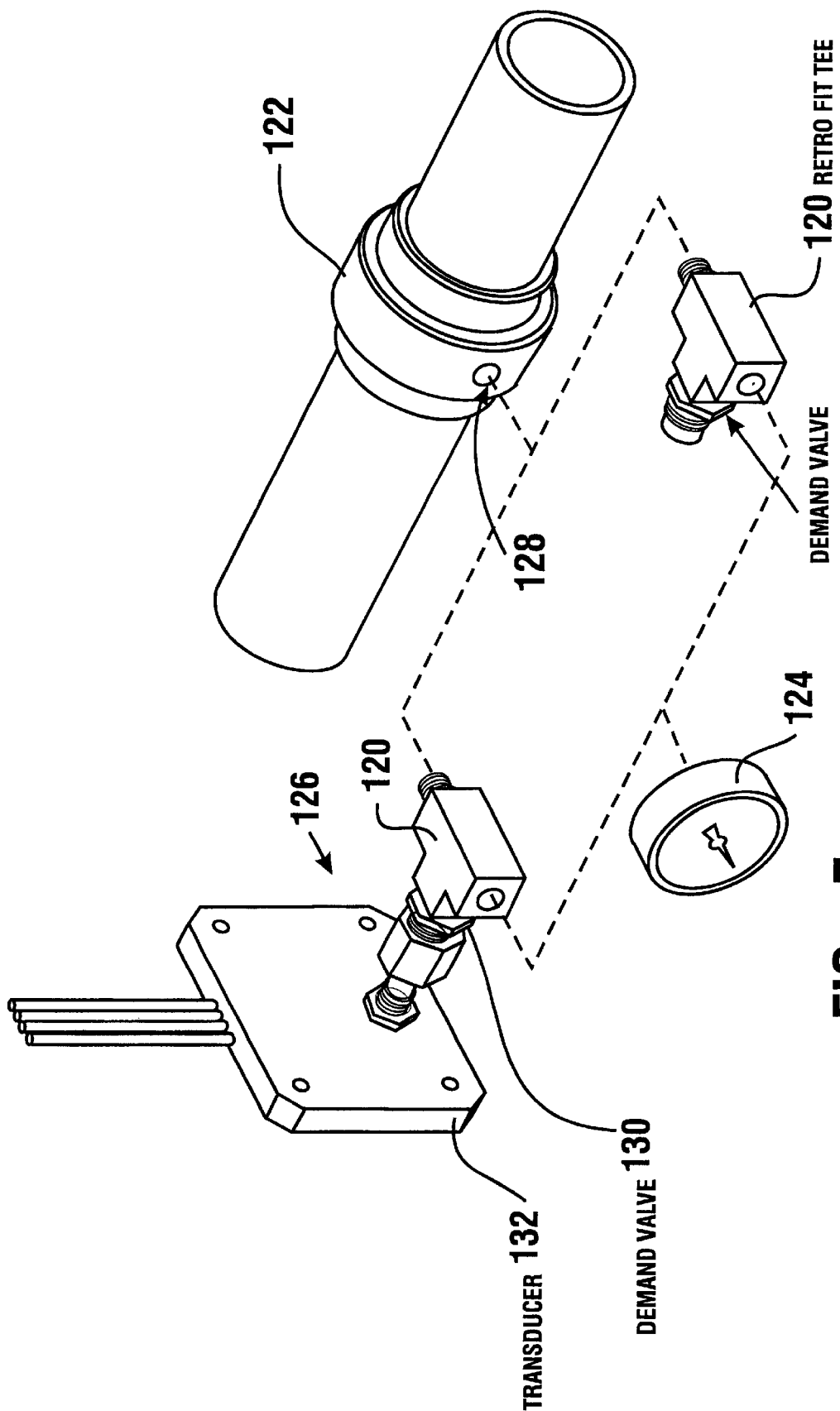
FIG. 7 is an exemplary schematic diagram representative of a transducer port retrofit assembly.

The present invention also encompasses retrofitting existing medical gas supplies to include one or more transducers. As shown in FIG. 7 a retrofit transducer assembly 126 may be adapted for placement between a preexisting gauge 124 and a gas conduit 122. In this described embodiment the preexisting gauge 124 may be removed from a gauge port 128 of the conduit 122 and the transducer assembly 126 may be threaded in its place. The transducer assembly includes a tee connector 120 that is adapted to be threaded into the gauge port 136 and is adapted to accept the connection of the original gauge 124. As previously described the exemplary transducer assembly 126 further includes a demand check valve 130 and at least one transducer 132.

Configuring the exemplary control panel 10 to include remote transducers, enables transducers be more easily found, replaced, and maintained. Also the labeling of the exemplary embodiment of the control panel further facilities the identification of those areas, rooms, and/or zones which are being monitored by each transducer.

The exemplary embodiment of the invention includes particular structures to achieve the desirable results. Those having skill in the art may devise other embodiments with other structures which employ the same inventive principles encompassed by the subject matter as claimed.

Thus the exemplary embodiment of the present invention achieves the above stated objectives, eliminates difficulties encountered in the prior methods, solves problems and attains the desirable results described herein.

In the foregoing description certain terms have been used for brevity, clarity and understanding. However, no unnecessary limitations are to be implied therefrom. Such terms are for descriptive purposes and are intended to be broadly construed. The descriptions and illustrations herein are by way of examples and the invention is not limited to the exact details shown and described.

In the following claims any feature described as a means for performing a function shall be construed as encompassing any means capable of performing the recited function. The means shall not be limited to the particular means shown as performing that function in the foregoing description or mere equivalents thereof.

Having described the features, discoveries and principles of the invention, the manner in which it is constructed and operated, and the advantages and useful results attained; the new and useful structures, devices, elements, arrangements, parts, combinations, systems, operations, methods and relationships are set forth in the appended claims.

We claim:

1. A system for suppling an uninterrupted supply of medical gases without backfeeding comprising
　at least one primary gas inlet;
　at least one gas outlet; and
　a control panel in operative fluid connection between the primary gas inlet and the gas outlet, wherein the control panel includes:
　　a shut-off valve in operative fluid connection between the primary gas inlet and the gas outlet; and
　　a secondary gas inlet port in operative fluid connection between the shut-off valve and the gas outlet, wherein the secondary gas inlet port is operatively configured to prevent fluid from flowing out of the system through the secondary gas inlet port, and wherein the secondary gas inlet port includes a gas specific threaded coupler.

2. The system according to claim 1, wherein the control panel further includes an opening and a movable face, wherein the face is adapted to close the opening when the shut-off valve is open, and wherein the face is not operative to close the opening when the shut-off valve is closed.

3. The system according to claim 2, wherein the shut off-valve includes a rotatable handle, wherein when the shut-off valve is closed, the rotatable handle extends through the opening of the control panel.

4. The system according to claim 2, wherein the control panel includes a gas pressure gauge in fluid connection between the shut-off valve and the gas outlet port, wherein the gas pressure gauge is viewable through the face.

5. The system according to claim 1 wherein the secondary gas inlet port includes a gas specific DISS threaded coupler.

6. The system according to claim 1 wherein the secondary gas inlet port includes a demand check valve.

7. The system according to claim 6 wherein the secondary gas inlet port includes a cap that is cooperatively threaded to mount to the gas specific threaded coupler.

8. The system according to claim 1 wherein the gas specific threaded coupler is adapted to accept a connection with a secondary gas supply, and wherein the secondary gas inlet is operative to enable fluid to flow into the system from the secondary gas supply.

9. The system according to claim 8, wherein the secondary gas inlet port is further adapted to accept a connection to at least one transducer.

10. The system according to claim 1, wherein the control panel further includes a transducer in fluid connection between the shut-off valve and the gas outlet.

11. The system according to claim 1, further comprising a second primary gas inlet and a second gas outlet, wherein the control panel further includes:

a second shut-off valve in fluid connection between the second primary gas inlet and the second gas outlet; and a second secondary gas input port in fluid connection between the second shut-off valve and the second gas outlet, wherein the second secondary gas inlet port is operatively configured to enable fluid to flow only into the system, and wherein the second secondary gas inlet port includes a second gas specific threaded coupler.

12. The system according to claim 11, wherein the second gas specific threaded coupler is operative to accept a connection to a different gas supply coupler than the first gas specific threaded coupler.

13. The system according to claim 11, wherein the control panel further includes an opening and a moveable face, wherein the face is operative to close the opening when both the first and second shut-off valves are open, and wherein the face is not operative to close the opening when either the first or second shut-off valves is closed.

14. The system according to claim 13, wherein the control panel includes a first pressure gauge and a second pressure gauge, wherein the first pressure gauge is in fluid connection between the first shut-off valve and the first gas outlet and the second pressure gauge is in fluid connection between the second shut-off valve and the second gas outlet, wherein both the first and second pressure gauges are viewable through the face, and wherein the face is operative to hold at least one gas identification placard adjacent each of the first and second pressure gauges.

15. A method of providing a secondary gas source for a medical gas delivery system including at least one primary gas source, shut-off valve, pressure regulator, check valve, pressure gauge, piping and at least one outlet port, comprising:

a) providing an inlet port adjacent the pressure gauge, wherein the inlet port includes a gas specific threaded coupler, a closure for the coupler and a check valve;

b) removing the closure for the threaded coupler of the inlet port;

c) connecting a secondary gas source to the specific threaded coupler, wherein the secondary gas source includes a pressure vessel, valve, regulator, hose and mating specific threaded coupler;

d) opening the valve on the pressure vessel;

e) delivering gas from the pressure vessel into said medical gas delivery system;

f) closing the shut-off valve of the medical gas delivery system; and g) controlling the pressure of gas applied from the pressure vessel into the medical gas system through use of the regulator associated with the pressure vessel.

16. The method according to claim 15 wherein said medical gas delivery system includes a plurality of individual primary gas sources, shut-off valves, pressure regulators, check valves, pressure gauges, piping and outlet ports, wherein step (a) further comprises providing an inlet port for each primary gas source, wherein the inlet port includes a different specific threaded coupler for each primary gas source.

17. The method according to claim 16 wherein step (c) further comprises connecting one of a plurality of secondary gas sources to one of the specific threaded couplers through a mating specific threaded coupler.

* * * * *

UNITED STATES PATENT AND TRADEMARK OFFICE
CERTIFICATE OF CORRECTION

PATENT NO.   : 6,305,400 B1
DATED        : October 23, 2001
INVENTOR(S)  : Donald M. Simo et al.

It is certified that error appears in the above-identified patent and that said Letters Patent is hereby corrected as shown below:

<u>Title page,</u>
Insert -- Related U.S. Application Data: Provisional application No. 60/150,252, Aug. 23, 1999. --.

<u>Column 1,</u>
Before line 1, insert
-- CROSS REFERENCE TO RELATED APPLICATIONS
    This application claims the benefit of U.S. Provisional Application Serial No. 60/150,252 filed Aug. 23, 1999. --.

Signed and Sealed this

Thirtieth Day of April, 2002

*Attest:*

*Attesting Officer*

JAMES E. ROGAN
*Director of the United States Patent and Trademark Office*

UNITED STATES PATENT AND TRADEMARK OFFICE
Certificate

Patent No. 6,305,400 B1                                  Patented: October 23, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Donald M. Simo, Vermilion, OH (US); James L. Lucas, Jr., Elyria, OH (US); and Paul R. Eagan, Milton, FL (US).

Signed and Sealed this Third Day of April 2007.

*ERIC KEASEL*
*Supervisory Patent Examiner*
*Art Unit 3753*